Figure 1:
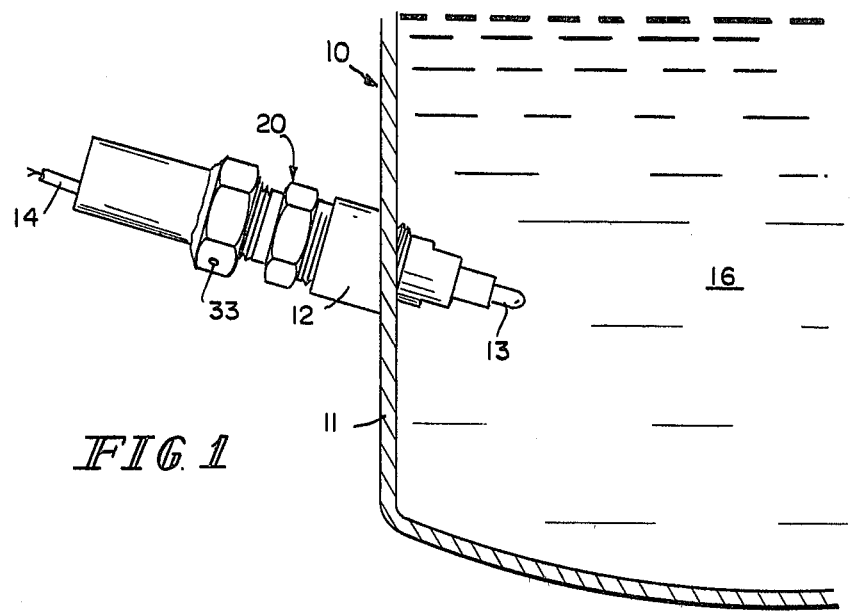

United States Patent [19]

Squires

[11] 4,309,506

[45] Jan. 5, 1982

[54] FERMENTATION SYSTEM AND FAILURE-DETECTION PROBE HOLDER

[75] Inventor: Robert W. Squires, Indianapolis, Ind.

[73] Assignee: Eli Lilly and Company, Indianapolis, Ind.

[21] Appl. No.: 158,584

[22] Filed: Jun. 11, 1980

[51] Int. Cl.³ .............................................. C12M 1/34
[52] U.S. Cl. ................................... 435/291; 435/287; 435/289; 435/290
[58] Field of Search .................... 435/3, 287, 289, 290, 435/291, 313, 314, 315, 316, 317, 807, 808, 817

[56] References Cited

U.S. PATENT DOCUMENTS 3,954,565  5/1976  Bocko et al. .................... 435/291 X
4,021,120  5/1977  Muller et al. .................... 435/808 X

OTHER PUBLICATIONS

Dr. Ingold, Specification E 764-31B/70, 1963 Zurich, Switzerland, p. 2096, distributed by Chemapec, Inc., Hoboken, New Jersey.
Dr. Ingold, E-764-20 Pressurized Straight Flow Assembly Unit, 764-20/764-31. Distributed by Chemapec, Inc., Hoboken, New Jersey.
Dr. W. Ingold, "Pressurized Elbow Flow Assembly Unit", 712-11/764-32.
Dr. Ingold, E764-INF "Industrial pH Measurement Using Pressurized Immersion Assemblies," Distributed by Chemapec, Inc., Hoboken, New Jersey, pp. 1-2.
"Ingold Threaded Nipples, Blind Plugs and Protector Shields," Distributed by Chemapec, Inc., Hoboken, New Jersey, pp. 1-5.
Arthur H. Thomas Company, *Scientific Apparatus and Reagents,* Nov. 1968, vol. 5, No. 1, pp. 1-4.

*Primary Examiner*—Robert J. Warden
*Attorney, Agent, or Firm*—Jenkins, Coffey, Hyland, Badger & Conard

[57] ABSTRACT

A system for the preparation of biological agents can include a vessel in which the biological agents are fermented and in which the fermentation is monitored by a probe detection means. Probe support means are fastened to the wall of the vessel to support the probe detection means with its operative end within the vessel and to provide access from outside the vessel to the output of the probe detection means. The probe support means has a seal-engaging surface at its forwardmost end within the tank. A seal is seated on the probe detection means forwardly of probe support means, and a seal compression member is fastened to the probe support means to compress the seal between the seal-engaging surface of the probe support means, the seal compression means, and the outer surface of the probe detection means to limit the collection of fermentation material to the exposed outer surfaces of the system and permit cleansing and sterilization of the system. The probe-support means is provided with an open passageway leading from behind the seal to outside of the vessel to permit detection of failure of the system.

5 Claims, 2 Drawing Figures

U.S. Patent   Jan. 5, 1982   4,309,506

FERMENTATION SYSTEM AND FAILURE-DETECTION PROBE HOLDER

This invention relates to an improved system for the preparation of biological agents that limits biological materials to outwardly exposed surfaces of the system and permits detection of failure of the system so that the system may be maintained to preclude contamination of materials in production.

A number of biological agents are prepared by processes involving fermentation and must be manufactured in batches. Examples include such materials as penicillin and tylosin, a Lilly agricultural product for the medication of respiratory diseases in chickens. Such biological agents are most commonly prepared by processes in which materials are fermented in large tanks. The fermentation processes must be closely controlled and the systems used in these processes include detection means or probe electrodes which extend into the materials being fermented within the tank to permit monitoring of the fermentation process.

Probe detector means may include pH and dissolved oxygen electrodes, ionic-type probes, and enzymatic probes. During the preparation of a batch of biological agents, such probe detection means may be used to monitor the process. Upon the completion of the preparation of one batch of agents or pharmaceuticals, it is necessary to sterilize the system in which they were prepared in order that a new batch may be prepared without contamination. Spores and bacteria that may remain from a completed batch, if not killed and removed from the system, can grow and contaminate a subsequent batch.

The systems known before this inventon included recesses, where the probe detection means entered the fermentation tank, that became contaminated with spores and bacteria and that were difficult to cleanse and sterilize. In some such systems, a seal, such as an O-ring, was provided at the inner bore of the probe detector support means near its end within the fermentation tank. Such O-ring seals were carried within an O-ring groove located a fraction of an inch inwardly from its end. These prior systems relied upon the slight compression of the O-ring seal between the outer surface of the electrode and the bottom of the O-ring groove. The seal did not satisfactorily preclude and seal against the collection of bacteria and spores in the system, and it included recesses between the forwardmost end of the probe detector support means and the electrode and between the O-ring groove and the O-ring and provided significant collection sites for spores and bacteria which could not be satisfactorily cleansed and sterilized.

The system of this invention has no significant sites in which spores and bacteria may collect that may not be cleansed and sterilized. The system provides sealed probe detection means that precludes fermentation materials from bypassing the seal, that substantially eliminates any recesses that are exposed to the fermentation materials, and that provides a simple means to detect when the system has failed and must be serviced before further use to avoid contamination of subsequently manufactured biological agents. In the system, the probe detector carries a seal seated on the probe detector outer surface forwardly of the probe detector support means. A seal compression member is fastened to the forward surface of the probe detector support means in such a manner that the seal is compressed between the forwardmost surface of the probe detector support means, the outer surface of the probe, and the seal compression member, to seal the system and substantially eliminate recesses. The probe detector support means includes an open passageway from behind the seal to its outer surface.

A system of the invention may include a tank or conduit, or other such vessel in which biological agents are produced with openings in the wall of the vessel for the insertion of probe detection means to monitor the process. Probe detection means may be ionic or enzymatic probes or electrodes for the determination of pH and dissolved oxygen or other such process parameter monitors. A probe support means adapted to be fastened to the vessel wall includes an inner bore adapted to receive the probe detection means. When in place in the system, the probe support means carries the probe detection means in such a manner that the operative end of the probe detection means extends from the probe support means within the vessel. A compressible seal or gasket, such as an O-ring, may be placed about the outer surface of the probe detection means; and a seal compression member can be placed about the probe and fastened on the probe support means to compress the seal between it, the seal-engaging surface of the probe support means and the outer surface of the probe detection means. In such a system, the probe detection means is sealed and an annular gap between the outer surface of the probe and the seal compression member can be precluded. Detection of failure of this system is provided, in accordance with the invention, by a small bore between the inner bore and an outer surface of the probe support means outside of the vessel.

Further features and advantages of this invention will be apparent from the following description and drawings in which:

FIG. 1 is a partial cross-sectional view of a system of this invention taken through the wall of a fermentation tank and showing the probe detection means and probe support means; and FIG. 2 is a partial cross-sectional view of the probe detector support means at a plane through its central axis and showing the manner of its support and sealing engagement with a probe electrode means and the system failure detection means.

A system of this invention is illustrated in FIG. 1. Such a system includes a vessel, such as tank 10 formed by a tank wall 11 to contain a biological agent 16 which is subjected to processing as, for example, by fermentation. The process, as experienced by the biological agent 16, is monitored by the operative end of a probe detection means 13 within the tank. The probe detection means 13 may be any means to detect or monitor parameters of the process within the tank. Examples of such probe detection means may be electrodes for monitoring the pH and the dissolved oxygen content of material 16 within the tank as it is being processed. The probe 13 is supported in a fitting 12 in the wall 11 of a tank by a probe detector, or electrode, support means 20. The probe detector support means 20 supports the detector 13 so that its operative end is exposed to the material 16 being processed within the tank and the probe output means 14 extends outwardly of the tank to permit the signal from the detector to be monitored. Although the operation of a probe detection means is frequently monitored by means of an electrical signal imposed upon conductors leading to the operative portion of an electrode, monitoring of the contents of the tank and the advantages of this invention are not limited to electrodes that are so monitored. The operation of the system and the need for service and special cleansing can be determined by observation of opening 33 as explained below.

Figure 2:
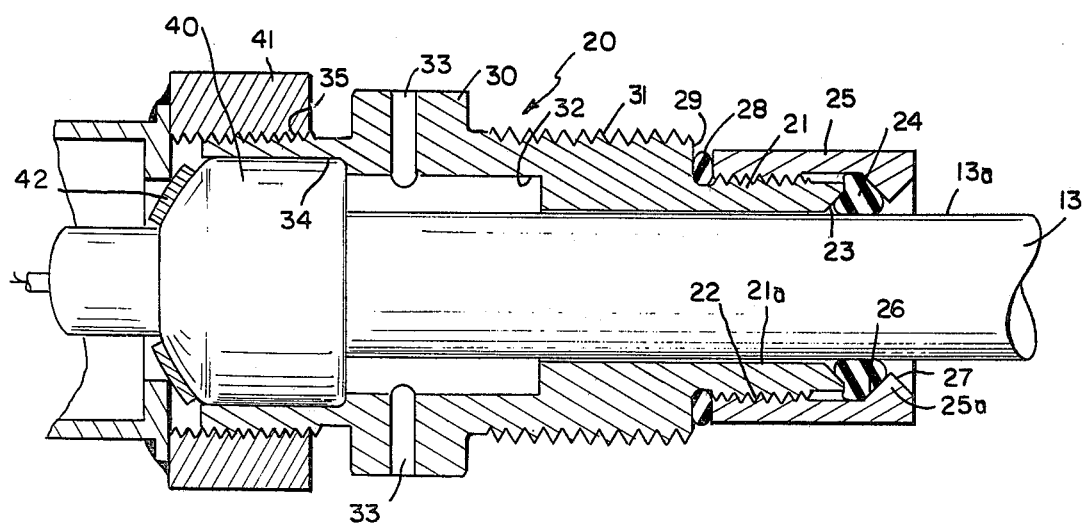

FIG. 2 shows the probe detector holder of this invention in substantially greater detail through a cross-sectional view of the probe support means 20, and the elements associated therewith, taken along a plane through their central axes. The detector 13 is not shown in cross section in FIG. 2 to avoid unnecessary detail.

As shown in FIG. 2, the probe support means 20 can have a cylindrical inner member 21 having an inner bore 21a adapted to receive the detector and a threaded outer surface 22. At the end of the probe support means 20 within the tank, is a seal-engaging surface 23, shown in FIG. 2 as a concave, frustoconical, seal-engaging surface formed in the forwardmost end of the inner member 21. A seal 24 is placed over the outer surface 13a of the detector 13 just forwardly of the probe support means 20. A seal compression member 25, such as the special flanged nut shown in FIG. 2, is threaded onto the outer surface 22 of the probe support means 20, thereby compressing the seal 24 between seal compression member 25, the forwardmost seal-engaging surface 23 of the probe support member 20 and the outer surface 13a of the detector 13. In its preferred embodiment, the seal compression member 25 is provided with an annular flange 25a having an inner seal-engaging surface 26 and an outer annular gap-precluding surface 27. As shown, the annular flange 25a has a concave, frustoconical, seal-engaging surface 26 within the annular flange 25a and a concave, frustoconical surface 27 on the outside surface of the annular flange 25a to provide a line intersection between the surface 26 and 27 so that, upon compression of the seal, it may be urged to the annular gap between seal compression member 25 and the outer surface of the probe 13, thereby sealing the forward portion of the probe support means and substantially eliminating any recess that may be difficult to clean and sterilize.

The probe support means 20 also provides, in accordance with the invention, means to detect a failure of the system and the need for repair and special cleansing to avoid contamination of materials in its subsequent use. An opening 33 is formed in the probe support means 20 to provide an open passageway leading from the space in the inner bore 21a behind the seal 24 to an outer surface of the probe support means 20 that is located outside of the vessel. In the embodiment of FIG. 2, the opening is a small bore with a diameter of a fraction of an inch, for example, 1/16 to ⅛ of an inch, that is formed transversely of the central axis of the probe support means 20, with the probe support portion 31 that engages the fitting 12 being located between the opening 33 and the seal 24.

In addition to the first seal 24, a second seal 28 may be carried by the probe support means 20 rearwardly of the threaded surface 22; and probe support means 20 may be provided with an extending surface, or boss 29. Seal compression member 25, the forwardmost inner portion 21 of probe support means, and its threaded outer surface 22 may be adapted so that, as the seal compression means 25 is threaded onto the inner portion 21 of the probe support means 20, the second seal 28 is compressed between the distal end 25b of the seal compression member 25 and the boss-like surface 29 of the probe support means, thereby compressing the second seal 28 to substantially preclude the formation of a recess between the seal compression member 25 and the probe support means 20.

The probe support means 20 may form a housing 30 which is preferably provided with a threaded outer surface 31 adapted to be threaded into the fitting 12 in tank wall 11. The inner member, or portion 21, of the probe support means 20 extending within the vessel may be a separate, cylindrical member that is pressed into and welded to the housing 30; however, the housing 30 and inner portion 21 may be machined from a single piece of material as shown in FIG. 2. Where housing 30 and the inner member 21 are separate pieces, the second seal 28 is located to preclude fermentation material from penetrating their interface.

The housing 30 has a housing inner bore 32 and is provided with the opening 33, permitting detection of failure of seal 24 and the system. The outer end of the housing inner bore 32 may be provided with a grommet-seating surface 34, and the housing may be provided with a second threaded outer surface 35 surrounding the grommet-seating surface 34. With this arrangement, the detector 13 may be inserted within a grommet 40 before it is placed within the probe support means 20. A grommet compression nut 41 may be threaded onto the second threaded outer surface 35 of the housing 30 to compress the grommet 40 against the grommet-seating surface 34 and outer surface of the detector 13, thereby supporting the probe 13 within the probe support means 21. A washer 42 may be provided between the grommet 30 and the grommet compression nut 41 to more evenly apply pressure to the grommet 40. The grommet compression nut 41 shown in FIG. 1 and FIG. 2 is intended for use with pH electrodes. Other members may be fitted to the probe support means 20 by the second threaded outer surface to accommodate dissolved oxygen electrodes or other types of probes.

A typical detector support for such a system can be made from stainless steel 316. The housing 30 can be turned from stainless steel 316 hexagonal bar stock of a sufficiently large and convenient size. The opening 33 can be formed by drilling a 3/32 inch bore through the housing 30 at right angles to its central angle, as shown in FIG. 2. The inner member 21 may be turned from cylindrical stainless steel bar stock to an outside diameter of about 0.687 inch and a length of about one inch. The inner bore 21a can have a diameter, for example, of 0.484 inch to receive a pH and dissolved oxygen electrode. The outer surface 22 may be provided with 11/16-20 threads located on the forwardmost half of its length. The threaded portion 22 can have a length of 5/16 of an inch beginning 150 of an inch from the end of the inner member 21. The inner member 21 may be pressed ½ inch into housing 30 and welded to provide a unitary probe support means 20. The forwardmost face of the inner member 21 can be provided with a frustoconical, seal-engaging surface 23 cut at an included angle of about 45° with respect to its central axis. The assembly of the inner member 21 with housing 30 can form an extended surface or boss 29 at the forwardmost surface of the housing 30. The seal compression member 25 is also made from stainless steel 316. It can be turned from around stock about ⅞ of an inch in diameter and provided with "flats" to permit the use of tools such as a wrench. The seal compression member 25 is provided with a central opening of 0.484 inch to permit it to be placed over a detector such as a pH and dissolved oxygen electrode. The seal compression member is also bored and threaded to provide 11/16-20 threads to mate the outer threaded portion 22 of the inner member 21. An annular flange 25a is formed at the forward portion of the seal compression member. The inner face 26 of the annular flange is turned at an included angle of about 45° with respect to its central axis to provide a concave, frustoconical, seal-engaging surface within the seal compression member and to form with the seal-engaging surface 23 of the inner member 21 a V-shaped cavity for the seal when the seal compression member 25 is threaded onto the inner member 21. In addition, the outer face of the annular flange 25a is turned at an included angle of about 30° with respect to its central axis to form a concave, frustoconical outer surface 27 that intersects the frustoconical inner surface 26 of the annular flange in, generally, a circular line thereby substantially eliminating any annular recess when the seal compression member 25 and the inner member 21 are assembled with a probe electrode. The length of the seal compression member is ½ inch so that its distal end 25b will lie closely adjacent the extended boss surface 29 of housing 30 when it is seated on the inner member 21. A second seal 28 placed rearwardly of the threaded outer surface 22 of the inner portion 21 adjacent the surface 29 of the probe support means 20 can thus be compressed between the seal compression member 25 and the surface 29.

Thus, in the system of the invention, probe detection means may be supported with its operative end exposed to a biological agent within a tank or conduit, and the system may be monitored for failure of its important components that seal and permit sterilization and cleaning of the system. Such systems may be useful not only in the production of pharmaceutical materials, but also in the commercial fermentation of yeast and in waste treatment systems.

While I have shown and described specific embodiments of the system of this invention, other embodiments may be devised without departing from the scope of the invention as set forth in the following claims.

What is claimed is:

1. A system for the preparation of biological agents, comprising
   a tank for the fermentation of biological agents;
   a threaded fitting in the tank wall;
   a detector to monitor the fermentation process;
   detector support means threadedly engaging the threaded fitting in the tank wall to support the operative portion of the detector within the tank and to provide access to the output of the detector outside of the vessel, said detector support means comprising
   a detector support housing adapted to receive and support the detector and having an inner bore and carrying a seal at the end of the inner bore within the tank and having a first threaded outer surface portion to engage the threaded fitting in the tank wall, a sealable surface adjacent the end of the inner bore outside of the tank, and a second threaded outer surface surrounding the sealable surface;
   a seal for the detector and seated on the sealable surface of the housing; and
   a seal compression nut threaded onto the second threaded outer portion of the detector support means,
   said detector support means including a small bore that extends transversely between its inner bore and outer surface outside of the tank.

2. A system for the preparation of biological agents, comprising a vessel in which biological agents are prepared by fermentation and in which the fermentation process is monitored by a probe detection means, probe support means adapted to fasten to the wall of a vessel and to support the probe detection means with its operative end exposed to the material being fermented within the tank and to provide access from outside the tank to the output of the probe detection means, a seal seated on the probe detection means forwardly of probe support means, said probe support means having a cylindrical threaded portion and a seal-engaging surface at its end within the tank, and a seal compression member threadedly engaging the cylindrical threaded portion of the probe support means to compress the seal against the seal-engaging surface of the probe support means and the outer surface of the probe detection means to limit the collection of fermentation material to the exposed outer surfaces of the system and permit sterilization of the system inside of the vessel, said probe support means also providing an open passageway leading from rearwardly of said seal to a portion of its outer surface outside of the vessel to permit detection of failure of the system.

3. A system for the preparation of biological agents, comprising
   a vessel for the viological agents;
   an opening in the vessel wall;
   a detector to monitor the process in the vessel;
   detector support means engaging the opening in the vessel wall to support the operative portion of the detector within the vessel and provide access to the output of the detector outside of the vessel, said detector support means having an inner bore adapted to receive the probe, an outer portion adapted to engage the opening in the vessel wall, and an open passageway leading from the inner bore to another outer portion located outside of the vessel;
   a seal seated on the detector forwardly of the detector support means within the vessel;
   a seal compression member to compress the seal, said system thereby being adapted to limit biological materials to outwardly exposed surfaces of the system and to permit detection of failure of the system.

4. A detector support for systems for the preparation of biological agents, comprising
   detector support means adapted to engage the wall of a fermentation vessel to support the operative portion of a probe detector within the vessel and to provide access to the output of the detector outside of the vessel;
   said detector support means having an inner bore adapted to receive and support a probe detector and a seal-engaging surface at its end to be inserted within the vessel, and further having a portion adapted to engage the vessel wall, and an opening leading from the inner bore to the outer surface of the detector support means at its other end, said portion adapted to engage the vessel wall lying between the opening and the end to be inserted within the tank.

5. A system for the preparation of biological agents, comprising a vessel for the biological agents;
an opening in the vessel wall;
a detector to monitor the process in the vessel;
detector support means engaging the opening in the vessel wall to support the operative portion of the detector within the vessel and provide access to the output of the detector outside of the vessel, said detector support means comprising a housing adapted to engage the opening in the vessel wall and an outer member adapted to fasten to said housing, said housing and outer member forming an inner bore adapted to receive the probe, and an open passageway leading from the inner bore to an outer portion of the detection support means located outside of the vessel, a surface of the inner bore being adapted to permit engagement and support of the detector; and
a seal provided by the detector support means within the vessel to seal against the detector.

* * * * *

UNITED STATES PATENT AND TRADEMARK OFFICE
CERTIFICATE OF CORRECTION

PATENT NO. : 4,309,506
DATED : January 5, 1982
INVENTOR(S) : Robert W. Squires

It is certified that error appears in the above-identified patent and that said Letters Patent are hereby corrected as shown below:

Col. 4, line 54, delete "150" and insert therefor --1/8--.

In the claims:

Claim 3, line 3, delete "viological" and insert therefor --biological--.

Signed and Sealed this

Twenty-fifth Day of May 1982

[SEAL]

Attest:

GERALD J. MOSSINGHOFF

Attesting Officer          Commissioner of Patents and Trademarks